(12) United States Patent
Nakamura et al.

(10) Patent No.: US 7,808,625 B2
(45) Date of Patent: Oct. 5, 2010

(54) APERTURE VARIABLE INSPECTION OPTICAL SYSTEM AND COLOR FILTER EVALUATION PROCESS

(75) Inventors: Kenji Nakamura, Iga (JP); Hisashi Shiraiwa, Koka (JP)

(73) Assignee: Otsuka Electronics Co., Ltd., Osaka (JP)

( * ) Notice: Subject to any disclaimer, the term of this patent is extended or adjusted under 35 U.S.C. 154(b) by 412 days.

(21) Appl. No.: 11/896,041

(22) Filed: Aug. 29, 2007

(65) Prior Publication Data

US 2008/0055592 A1    Mar. 6, 2008

(30) Foreign Application Priority Data

Aug. 30, 2006   (JP) ............... 2006-234057

(51) Int. Cl.
  *G01J 1/00*   (2006.01)
  *G01N 21/00*  (2006.01)
(52) U.S. Cl. ...................... 356/123; 356/432
(58) Field of Classification Search ........ None
  See application file for complete search history.

(56) References Cited

U.S. PATENT DOCUMENTS 4,290,698 A * 9/1981 Milana ............... 356/600
5,045,296 A   9/1991 Pfeffer et al.
5,400,135 A * 3/1995 Maeda ............... 356/239.1

FOREIGN PATENT DOCUMENTS

| JP | 3-153506 | 7/1991 |
|---|---|---|
| JP | 6-18410 | 1/1994 |
| JP | 06-180425 | 6/1994 |
| JP | 11-264935 | 9/1999 |
| JP | 2000-121553 | 4/2000 |
| PL | P.364232 A1 | 5/2005 |
| PL | 191356 B1 | 5/2006 |

* cited by examiner

*Primary Examiner*—Gregory J Toatley, Jr.
*Assistant Examiner*—Amanda H Merlino
(74) *Attorney, Agent, or Firm*—Finnegan, Henderson, Farabow, Garrett & Dunner, L.L.P.

(57) ABSTRACT

Disclosed is an aperture variable inspection optical system including a variable aperture unit 13 having a polygonal light transparent section and light collecting systems 12*a*, 12*b* for forming an irradiation spot U of light passing through the variable aperture unit 13 at the position of a sample S. The variable aperture unit 13 is capable of changing the shape/size of the polygon. The size of the irradiation spot U can be changed without rearranging the aperture unit.

3 Claims, 10 Drawing Sheets

REFERENCE

APERTURE VARIABLE INSPECTION OPTICAL SYSTEM AND COLOR FILTER EVALUATION PROCESS

BACKGROUND OF THE INVENTION

1. Field of the Invention

The present invention relates to an inspection optical system that is suitably used for inspection of optical characteristics of color filters incorporated in liquid crystal display devices and the like.

2. Description of Related Art

A color filter for a liquid crystal display device generally consists of three color filters including R, G, and B. In this specification, the range covered by one R filter, the range covered by one G filter, and the range covered by one B filter are each defined as one pixel.

Evaluations of optical characteristics of this color filter are carried out such that a light spot from a measurement light source is projected onto the center of one pixel of R, transmittance spectrum, chromaticity, white balance, etc. of the central area are measured. The same measurements are made on the pixels of G and B. The color filter to be measured is referred to as the "sample".

Figure 14:
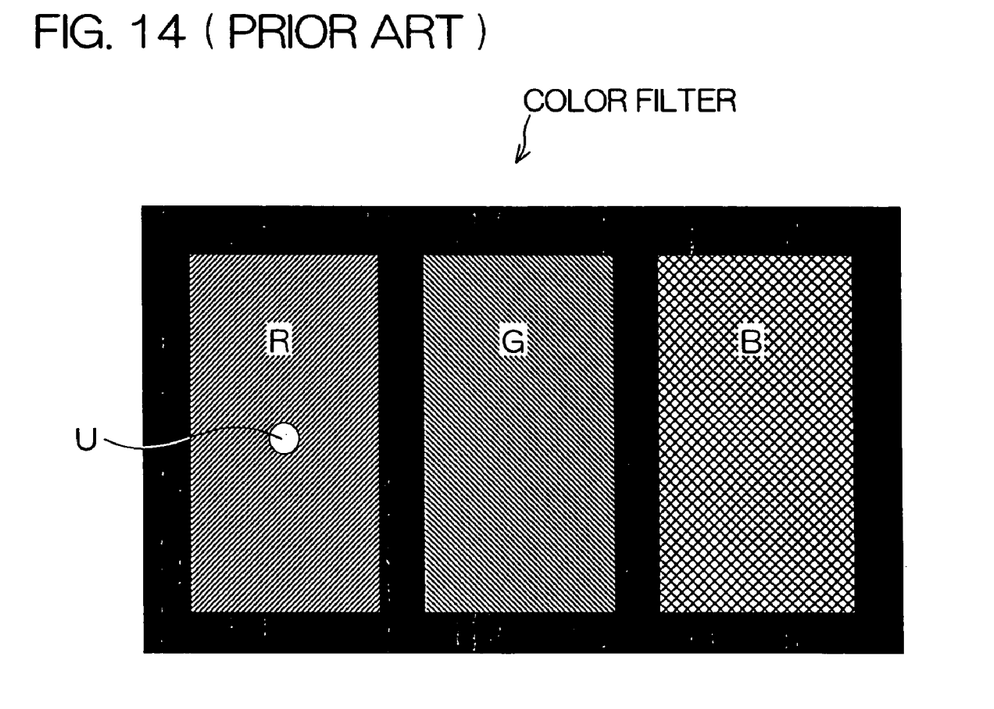
FIG. 14 shows a conventional irradiation spot U in a fixed size incident on a sample.

FIG. 14 shows an irradiation spot (referred to as "irradiation spot U") incident on one pixel (R pixel in this Figure).

As FIG. 14 shows, the irradiation spot U is smaller than the size of one pixel in conventional cases.

The reason that conventional measurements are carried out by projecting such an irradiation spot U smaller than the size of one pixel on a central area of the pixel is that the chromaticity/transmittance within the pixel of a color filter have been assumed to be approximately uniform.

Figure 15:
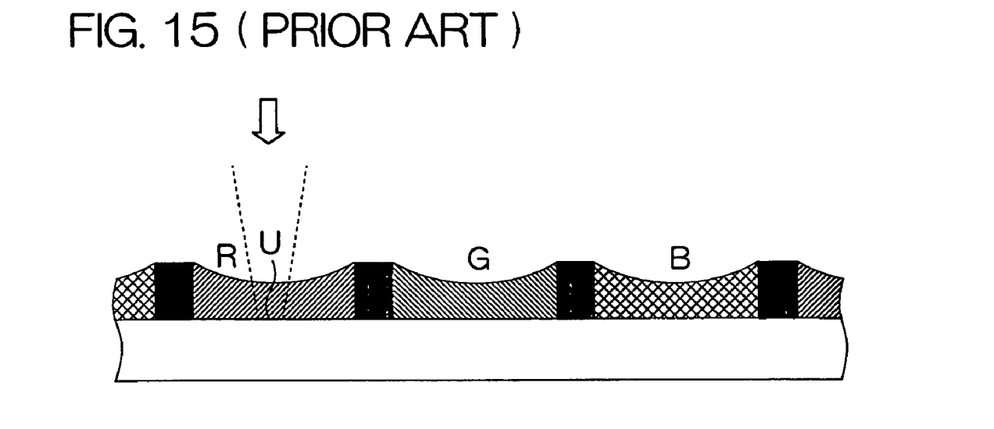
FIG. 15 is a cross-sectional view showing a thickness distribution of a color filter within one pixel.

However, recently, as the display screens of liquid crystal display devices become larger, the size of the pixel of a color filter becomes larger. With the increased size of pixel and changes in production process, the film thickness of the color filter within one pixel has become uneven as shown in a cross-sectional view of FIG. 15. Accordingly, unevenness in chromaticity/transmittance within the pixel of the color filter has been also pointed out, whereby the process of evaluating chromaticity/transmittance of a color filter needs to be reviewed.

In addition, only irradiation spots U with fixed sizes have been heretofore available.

In fact, since the pixel size of a color filter varies depending on the application of the products, the shape of the aperture that forms the irradiation spot needs to be changed accordingly.

In order to change the size of the irradiation spot U, it is necessary to replace the aperture unit inserted into the optical system, and readjustment of the optical system is required upon each replacement.

It is therefore an object of the present invention to provide an aperture variable inspection optical system that allows the size of the irradiation spot U to be changed without replacing the aperture unit.

It is another object of the present invention to provide a color filter evaluation process that enables inspection of optical characteristics of the entire area of one pixel of a color filter.

SUMMARY OF THE INVENTION

An aperture variable inspection optical system according to the present invention is an inspection optical system for optical measurement performed by projecting light of a measurement light source on a sample and receiving light from the sample, which comprises: a variable aperture unit including a light transparent section whose size is variable and a light collecting optical system for forming an irradiation spot of light that passes through the variable aperture unit at the position of the sample, wherein the variable aperture unit comprises a first aperture opening/closing mechanism including a couple of slide plates having edges opposed to each other and a second aperture opening/closing mechanism including another couple of slide plates having edges opposed to each other, and the first and second aperture opening/closing mechanisms are disposed so as to cross each other at a predetermined angle.

This arrangement enables formation of an irradiation spot in any size at the position of the sample. When the irradiation spot is formed so as to coincide with the entire area of one pixel, it is possible to measure optical characteristics of the entire area of one pixel. The shape of the irradiation spot can be automatically changed in accordance with the shape of any given pixel. In addition, it is not necessary to prepare a plurality of aperture units in different sizes for samples with different pixel sizes because the shape of the aperture can be adjusted at each measurement.

The arrangement may be such that one lever rotatable about a spindle is provided, and each of the both ends thereof is in contact with an edge of the first slide plate in its sliding direction and an edge of the second plate in its sliding direction, respectively, and a proximal end of the first slide plate is driven to slide by an actuator. In this case, when the proximal end of the first slide plate is driven to slide in one direction by the actuator, the lever rotates to move the second slide plate in the opposite direction. While the edges of the first and second slide plates can be moved in directions opposite to each other, the center line of the aperture can be assumed stationary at all times as long as the rotation angle of the lever is within a minute range.

When the proximal end of the second slide plate is biased by means of a spring, rattling of the second slide plate can be reduced, so that precision in shape of the aperture can be maintained.

In addition, when the arrangement is such that the foregoing couple of slide plates in the first aperture opening/closing mechanism are constituted of first and second slide plates, and the couple of slide plates in the second aperture opening/closing mechanism are constituted of third and forth slide plates, in which a principal surface of the first slide plate and a principal surface of the second slide plate are flush with each other on a plane and a principal surface of the third slide plate and a principal surface of the forth slide plate are flush with each other on a plane, and both of two planes are in contact with each other, an aperture with any desired shape can be formed by arranging two variable aperture units in tandem with each other. Furthermore, because of the foregoing two planes in contact with each other, the irradiation spot can have a sharp profile.

A color filter evaluation process according to the present invention is an evaluation process performed by projecting light of a measurement light source on a pixel of a sample color filter and receiving light from the sample for optical measurements thereof, which comprises the steps of: preparing a transparent plate including one pixel formed with a frame as a reference; adjusting the size of a transparent section by a variable aperture unit including the transparent section whose size is variable so that the profile of an irradiation spot of the measurement light source includes the entire area of the pixel; measuring an intensity R of light of the reference with the measurement light source being illuminated; preparing a color filter including one pixel formed with a frame as a sample; adjusting the size of the transparent section by the variable aperture unit so that the profile of an irradiation spot of the measurement light source includes the entire area of the pixel; measuring an intensity S of light of the sample with the measurement light source being illuminated; and calculating a ratio R/S, thereby determining a transmittance of the sample.

By this process, the irradiation spot projected on the pixel of a color filter can be formed to cover the BM (black matrix) so that the entire area of one pixel can be irradiated. Therefore, even in the case of a color filter in which chromaticity/transmittance are uneven within one pixel, chromaticity/transmittance of the entire area of one pixel can be evaluated. In addition, it is possible to form an irradiation spot in accordance with the shape of a pixel of any desired color filter.

When the chromaticity/transmittance of one pixel of a color filter are measured at one time, the transparent plate used as a reference may be a transparent plate before being coated with a color filter on which only the BM pattern is formed. Since accurate data cannot be obtained when the light transmitting area of one pixel of the reference is different from the light transmitting area of one pixel of the color filter, a transparent plate before being coated with a color filter that is formed with only the same BM pattern is used as the reference for evaluation.

These and other advantages, features and effects of the present invention will be apparent from the following description of preferred embodiments with reference to the accompanying drawings.

DETAILED DESCRIPTION OF PREFERRED EMBODIMENTS

Figure 1:
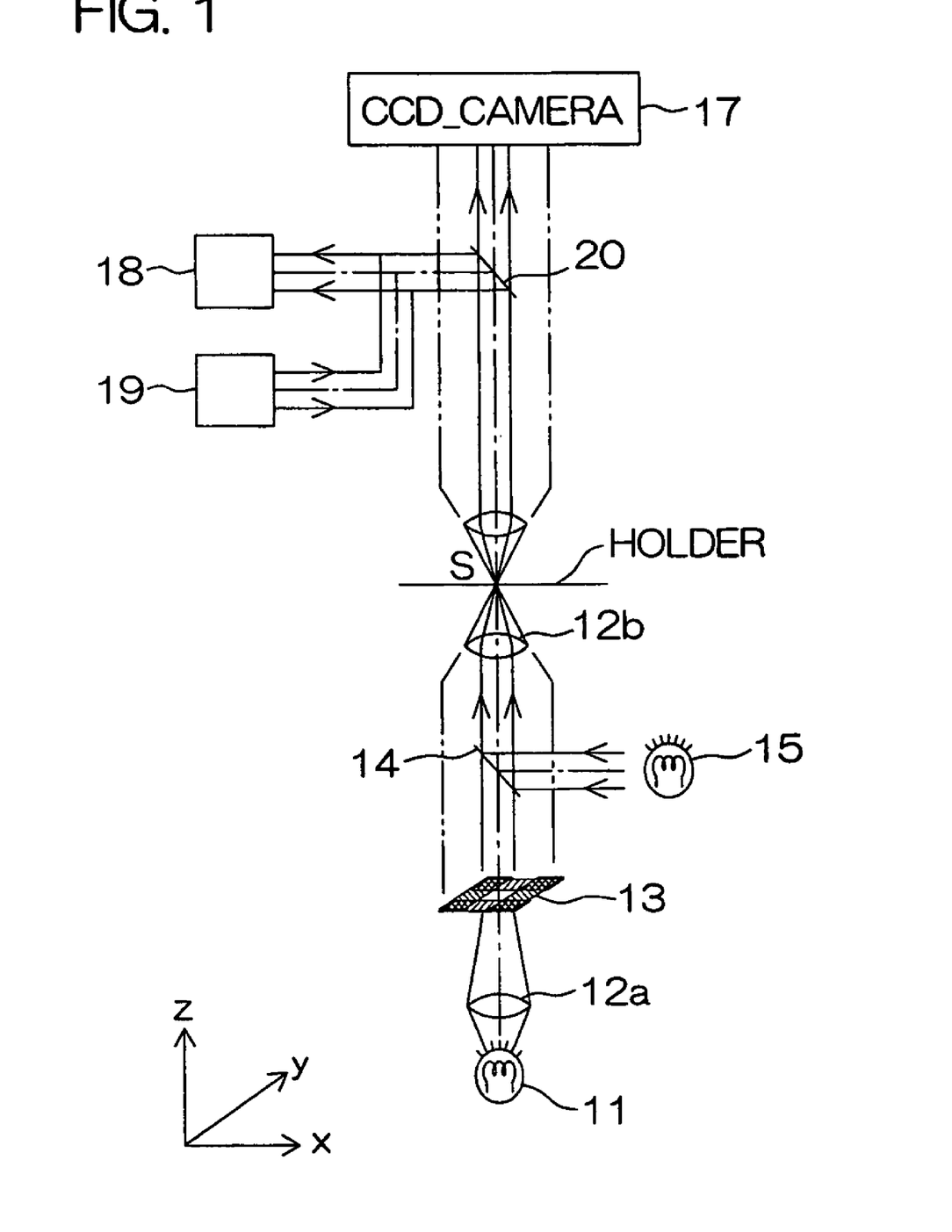
FIG. 1 is a schematic diagram showing the overall structure of an aperture variable inspection optical system.

FIG. 1 is a schematic diagram showing the overall structure of an aperture variable inspection optical system.

The aperture variable inspection optical system according to the present invention comprises a light projecting optical unit for projecting an irradiation spot on a sample S and a light receiving optical unit for receiving light transmitted through the sample S for measurement thereof.

The light projecting optical unit includes a transmittance measurement light source 11 for projecting light for measurement on the sample S, lens systems 12a, 12b for converging the light from the transmittance measurement light source 11 onto the sample S, a variable aperture unit 13 for forming a quadranglar aperture that is interposed between the transmittance measurement light source 11 and the sample S, a half mirror 14 interposed between the transmittance measurement light source 11 and the sample S, and a transmittance observation light source 15 for projecting light on the half mirror 14.

The light receiving optical unit includes a CCD camera 17 for capturing image of the sample S, a spectrometer 18 for spectral analysis of light transmitting through the sample S, an area marker 19 for projecting a light spot for positioning on the sample S, and a half mirror 20 for separating an optical axis directed to the CCD camera 17 from an optical axis directed to the spectrometer 18 and the area marker 19.

Let the direction of the optical axis of transmitted light beams connecting the transmission measurement light source 11, the variable aperture unit 13 and the lens systems 12a, 12b be represented by z, and directions orthogonal thereto be represented by x and y. An XY stage is situated between the light projecting optical unit and the light receiving optical unit, where a holder is disposed on which the sample S is mounted. The sample S can be freely moved in the X, Y directions by the XY stage.

Figure 2:
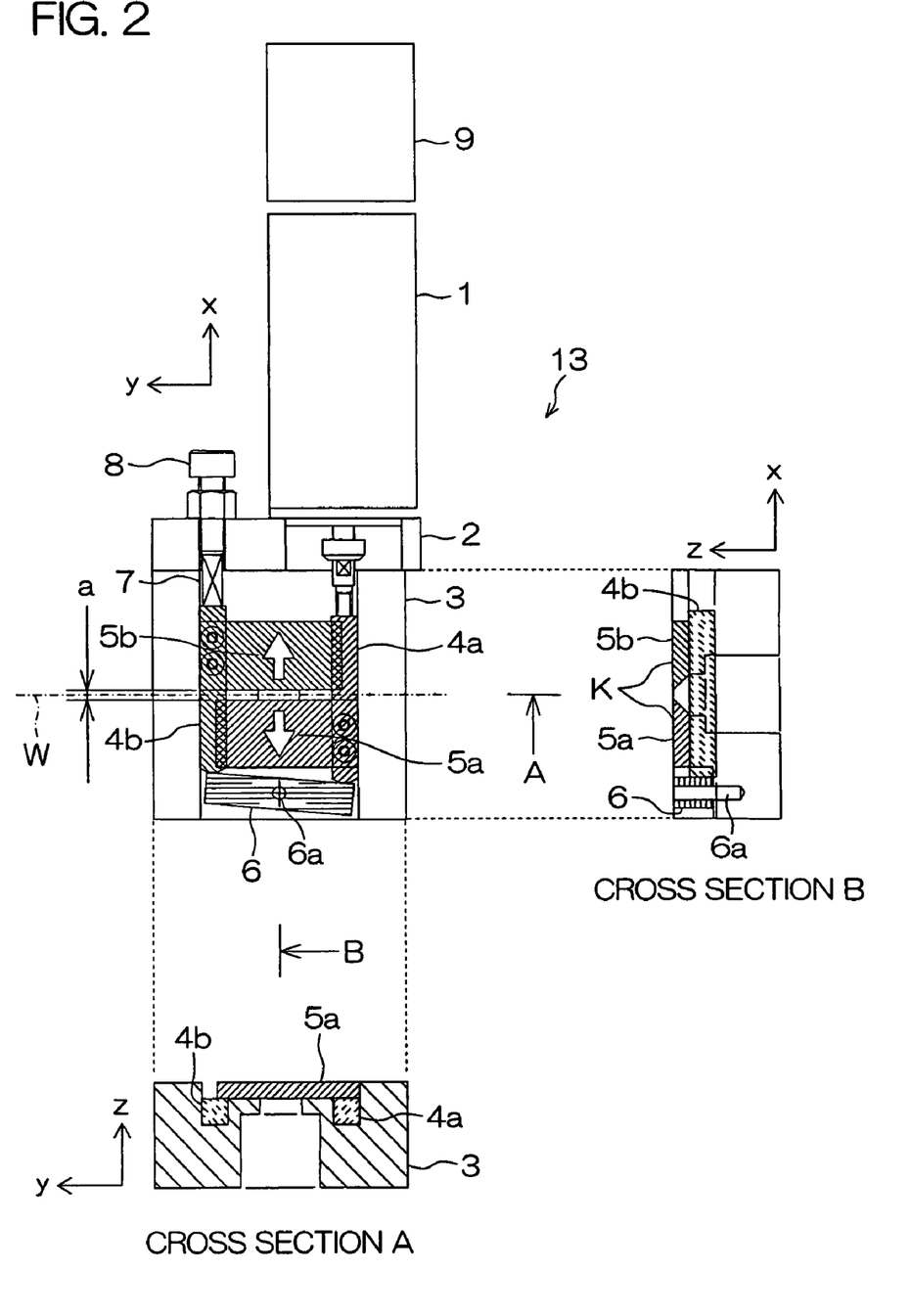
FIG. 2 is a plan view and a cross-section showing a detailed structure of an aperture opening/closing mechanism.

FIG. 2 is a plan view and a cross-section showing a detailed structure of an aperture opening/closing mechanism.

The aperture opening/closing mechanism includes a pulse-controlled electric actuator 1 whose head moves in the X direction, a motor base 2 and a body 3 in the form of a rectangular parallelepiped.

The body 3 includes a couple of guide grooves formed in parallel to each other along the x direction on an upper surface (a surface oriented to the z direction) thereof. Elongated guides 4a, 4b slidable along the X direction are placed in the guide grooves. The guides 4a, 4b are guided by the guide grooves on the body 3 to move in the x direction.

In addition, a couple of rectangular slide plates 5a, 5b for forming the aperture are mounted slidably in ±x directions on the upper surface of the body 3. The slide plate 5a is fixed with screws to the guide 4a, and the slide plate 5b is fixed with screws to the guide 4a.

The head of the electric actuator 1 is connected to an upper end (the end in the +x direction) of the guide 4a.

A pin 6a that forms a spindle along the optical axis, in other words, the z direction is provided in the lower part of the body 3, and a lever 6 with a hole through which the pin 6a penetrates in its central part is rotatably attached to the pin 6a. One end of the lever 6 is in contact with a lower end (the end in the −x direction) of the guide 4a, and another end of the lever 6 is in contact with a lower end (the end in the −x direction) of the guide 4b.

A stopper bolt 8 fixed to the body 3 is in contact with the upper end of the guide 4b through a spring 7. The spring 7 provides the guide 4b with an appropriate degree of resistance so as to eliminate play of the guide 4a.

Knife edges located on straight lines along the y direction are formed on the upper side of the slide plate 5a and on the lower side of the slide plate 5b, respectively, to face each other.

Furthermore, an encoder 9 for measuring travel distance of the head of the electric actuator 1 is connected to a rear end shaft of the electric actuator 1.

Now, the operation of this variable aperture unit 13 is described.

To open the aperture, the electric actuator 1 is pulse-driven to move the head in the −x direction. This causes the slide plate 5a to move downward.

In response to this movement, the lower end of the guide 4a presses one end of the lever 6 to lift the other end of the lever 6, thereby pressing the guide 4b upward. This movement causes the slide plate 5b to move in the +x direction.

The movements of these slide plates 5a, 5b in the −x direction and in the +x direction, respectively, cause the aperture to open equally upward and downward. The center line W (See FIG. 2) of the aperture can be assumed stationary at all times as long as the rotation angle of the lever 6 is within a minute range. The "minute range" refers to, for example, a range in which the rotation angle of the lever 6 is within ±10° from the level state.

To close the aperture, the electric actuator 1 is driven to move the head in the +x direction. The spring 7 whose one end is fixed to the stopper bolt 8 presses the slide plate 5b downward. This causes the lever 6 to rotate reversely to press the slide plate 5a upward. As a result, the aperture closes.

A structure of the aperture opening/closing mechanism in which the slide plates 5a, 5b are moved upward and downward (in ±x directions) has been described above. However, in order to project an irradiation spot of light transmitted through a quadrangular aperture onto the position of the sample S, another aperture opening/closing mechanism that opens/closes the aperture leftward and rightward (±y directions) is required.

This can be realized by providing an aperture opening/closing mechanism M2, which is the same as the aperture opening/closing mechanism M1 shown in FIG. 2, by rotationally moving it by 90° within the x-y plane.

Figure 3:
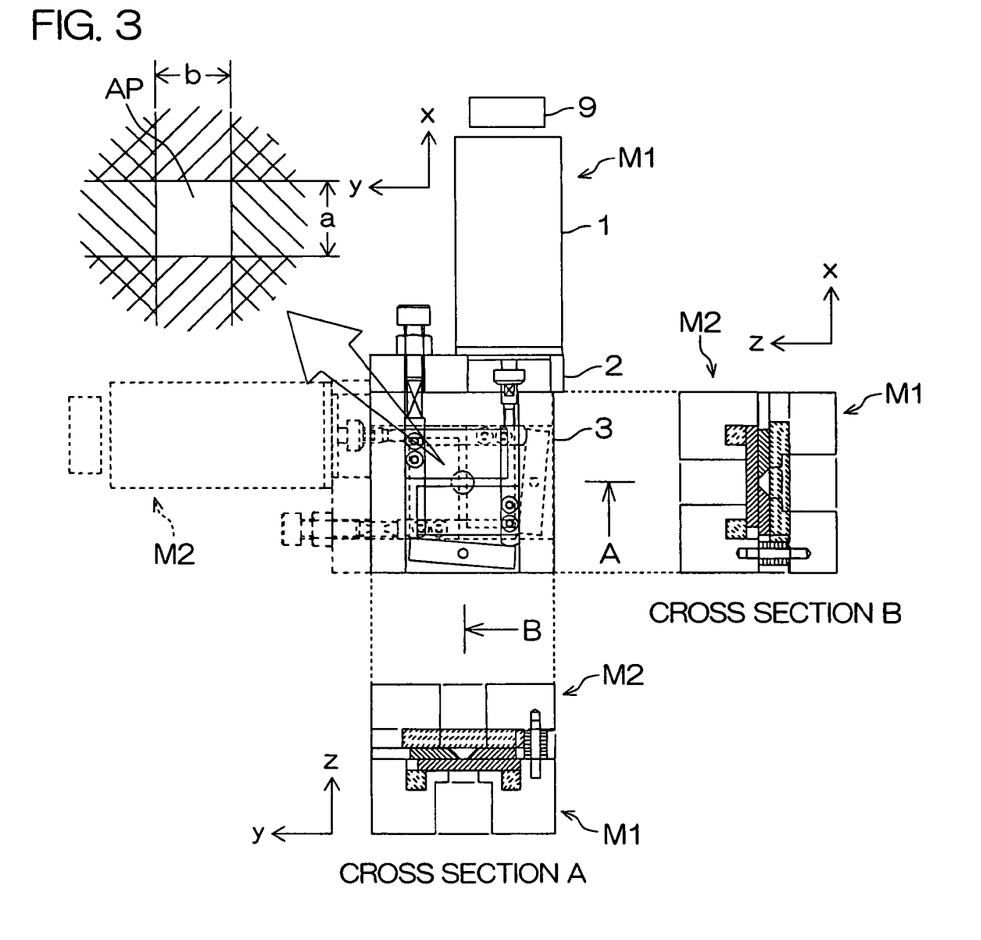
FIG. 3 is a plan view and a cross-section showing an arrangement including an aperture opening-closing mechanism M1 for opening/closing the aperture in a vertical direction (X) and another aperture opening/closing mechanism M2 for opening/closing the aperture in a horizontal direction (y) that is disposed to cross the aperture opening/closing mechanism M1 at 90°.

FIG. 3 is a plan view and a cross-section showing an arrangement including an aperture opening-closing mechanism M1 for opening/closing the aperture in a vertical direction (X) and an aperture opening/closing mechanism M2 for opening/closing the aperture in a horizontal direction (y) that is disposed to cross the aperture opening/closing mechanism M1 at 90°. The aperture opening/closing mechanism M2 is indicated in broken lines.

The slide plates of the aperture opening/closing mechanism M1 and the aperture opening/closing mechanism M2 are arranged in tandem in the z direction. By driving the electric actuator of the aperture opening/closing mechanism M1 and the electric actuator of aperture opening/closing mechanism M2, a quadrangular variable aperture AP as shown in FIG. 3 can be formed.

That is, suppose the length of a side of the quadrangle along the x direction be a, and the length of a side along the y direction be b, the length a can be freely determined by driving the electric actuator of the aperture opening/closing mechanism M1, and the length b can be freely determined by driving the electric actuator of the aperture opening/closing mechanism M2. Accordingly, the ratio between longer sides and shorter sides of the quadrangle can also be freely determined, allowing to change the shape/size of the quadrangle.

Figure 4:
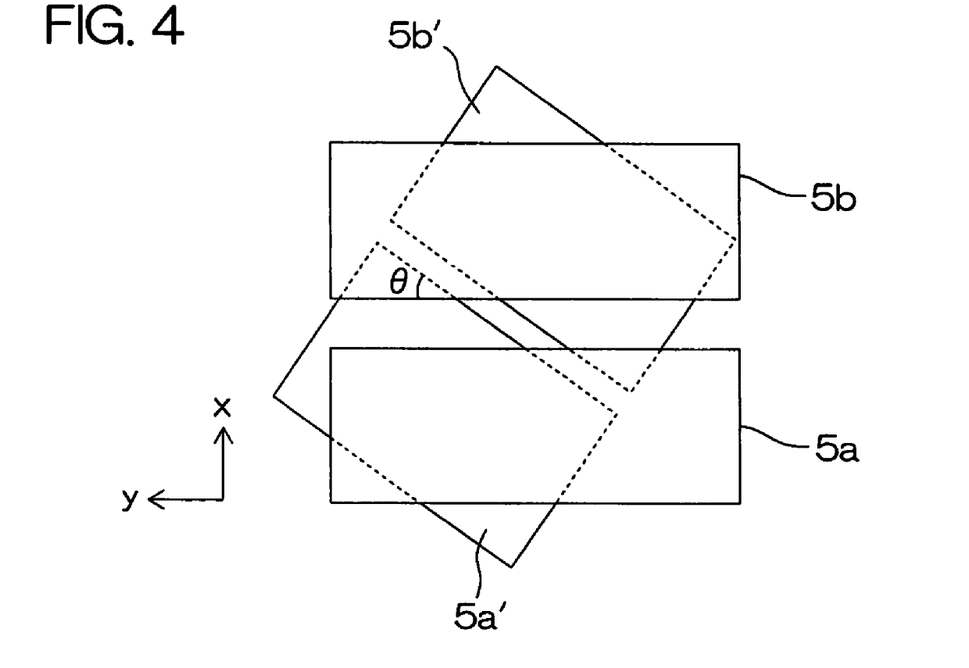
FIG. 4 is a plan view showing a state where slide plates of an aperture opening/closing mechanism M1 and an aperture opening/closing mechanism M2 are disposed to cross each other at an angle θ satisfying 0<θ<90°.
Figure 5:
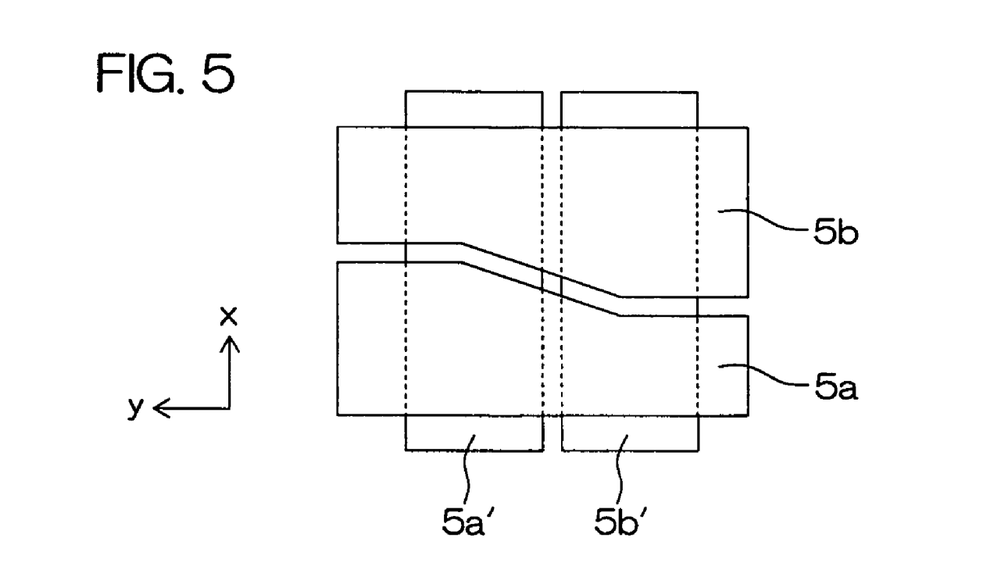
FIG. 5 is a plan view showing a state where the moving directions of slide plates are orthogonalized, and knife edges of the slide plates are formed to have parts inclined at arbitrary angles.
Figure 6:
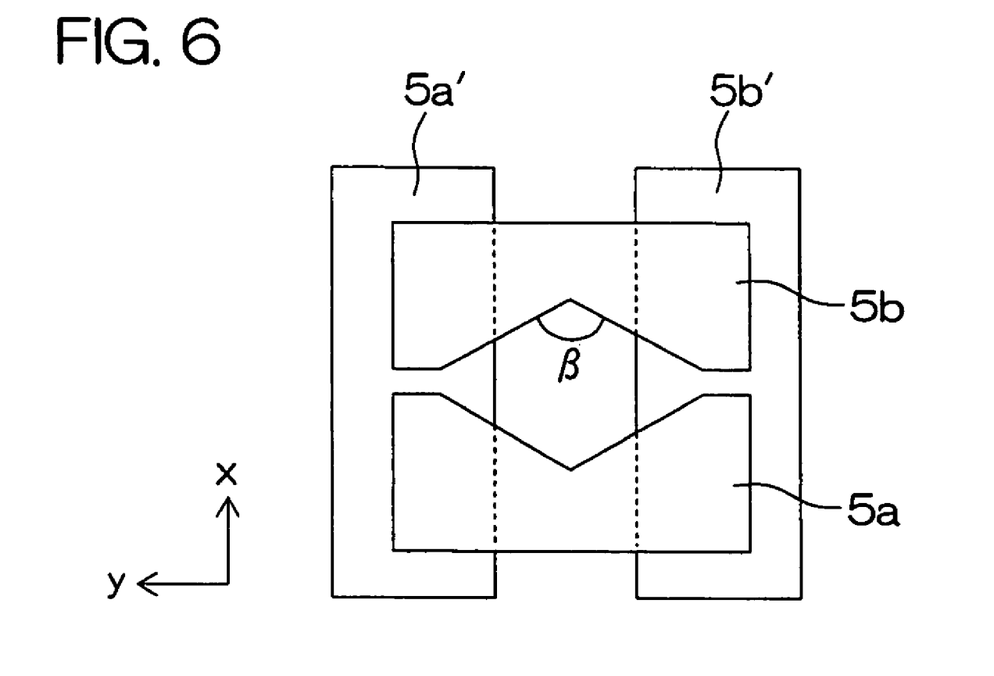
FIG. 6 is a plan view showing a state where the moving directions of slide plates are orthogonalized, and knife edges of the slide plates are formed to have parts angled at a predetermined angle.

While in this embodiment, the aperture opening/closing mechanisms M1 and M2 are disposed so that they cross at right angles, the degree of angle may not necessarily be 90°. For example, they may be disposed to cross at an angle θ satisfying 0<θ<90° as shown in FIG. 4. By disposing them to cross at an angle θ as described above, it is possible to form an aperture with a quadrangular shape having any given angles other than squares or rectangles. Alternatively, as shown in FIG. 5, where the moving directions of the slide plates are orthogonalized, the knife edges of slide plates on one side may be inclined at any given angle. Further, as shown in FIG. 6, the knife edges of slide plates on one side may be formed to have parts angled at an arbitrarily angle β (greater than 0° and smaller than 180°) so as to form a hexagonal irradiation spot. The arrangements shown in FIGS. 4-6 are effective in cases where the shape of the pixel to be inspected is not a square or rectangle, because an irradiation spot with a shape that fits to the pixel can be formed.

The slide plates are formed with knife edges (See cross section B in FIG. 2). When the slide plates are brought in proximity to each other, the knife edges form a V-shape cross section. The surface of a slide plate on the side where the distance between the knife edges is shorter is referred to as the "principal surface K". When the slide plates of the aperture opening/closing mechanism M1 and the slide plates of the aperture opening/closing mechanism M2 are arranged in tandem, it is preferred to dispose the principal surfaces K of the respective slide plates to be in contact with each other so as to obtain an irradiation spot with a sharp profile.

Figure 7:
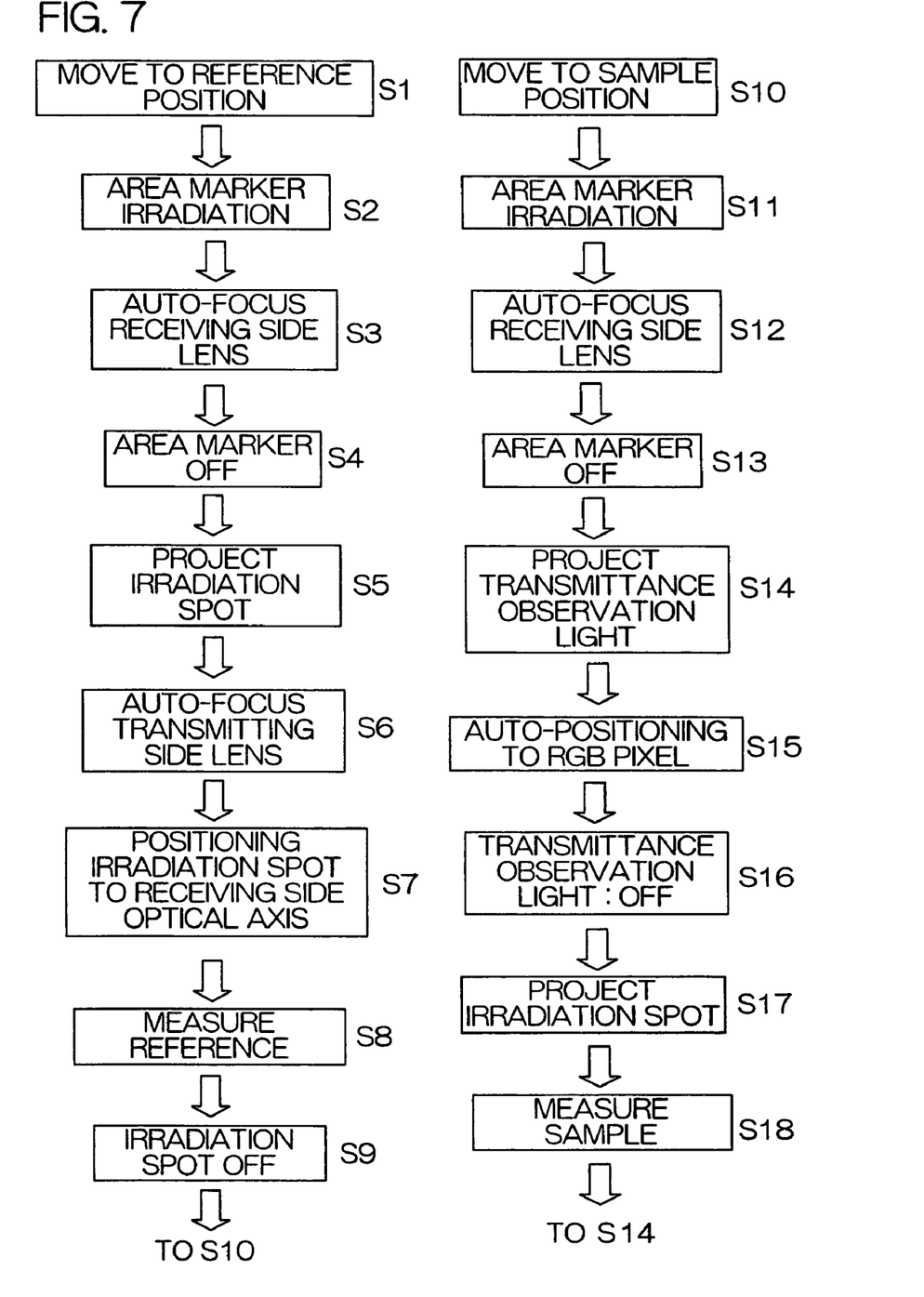
FIG. 7 is a flowchart for illustrating an operational procedure of an aperture variable inspection optical system.

Hereinafter, an operational procedure of this aperture variable inspection optical system will be described based on a flowchart (FIG. 7).

Here, a color filter attached to a liquid crystal display device is taken as an example of the sample to implement, a process of evaluating a color filter.

Figure 8:
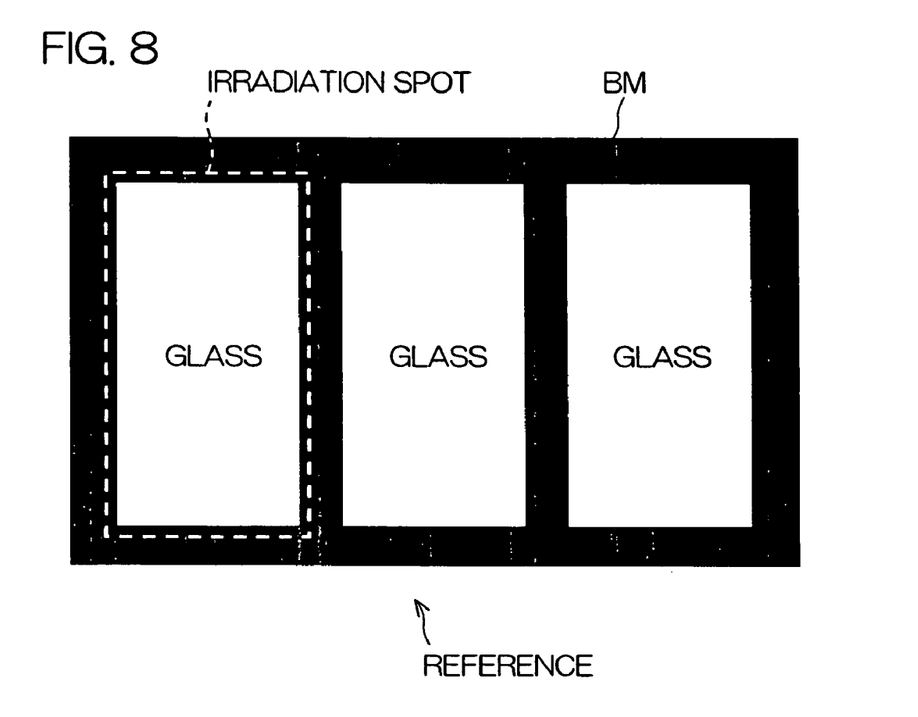
FIG. 8 is a plan view showing a transparent glass plate serving as a reference that is printed in a grid-like black matrix as a frame of each pixel.

First, as shown in FIG. 8, a transparent glass plate printed with a grid-like BM (black matrix) pattern is prepared. This is used as a reference.

In this case, since accurate measurement data cannot be obtained when the light transmitting area of one pixel of the reference is different from the light transmitting area of one pixel of the color filter, the BM pattern of the reference needs to be the same as the BM pattern of the color filter. Therefore, a glass plate before being coated with a color filter on which only the BM pattern is formed is preferably used. The size of one pixel is, for example, on the order of 90 μm×300 μm.

The aperture variable inspection optical system always includes a sample holder on which a sample can be placed, and a reference holder on which a reference that is at least as large as several tens of pixels can be placed. The sample holder and reference holder may be one holder divided into each holder, or individual holders.

First, the aperture variable inspection optical system is moved to the position of the reference holder (Step S1). Inspection light is projected from the area marker 19 (Step S2). With the lenses of CCD camera 17 and spectrometer 18 being autofocused, the XY stage is operated to move the pixel as the reference to a central position of the area marker 19 (Step S3), and the inspection light of the area marker 19 is turned off (Step S4). This enables the reference can be placed at the optical axis of the CCD camera 17 and spectrometer 18 in the light receiving optical unit.

Subsequently, the transmittance measurement light source 11 is turned on (Step S5), the lens systems 12a, 12b are auto-focused (Step S6). Thereafter, the irradiation spot is positioned to the optical axis (Step S7). This positioning is carried out such that, during observation of the CCD camera 17, the pixel to be the reference is brought to the central position of the screen of the CCD camera 17.

Then, the variable aperture unit 13 is controlled to determine the shape (dimensions a, b) of the irradiation spot so that the profile of the irradiation spot covers the frame of one pixel, i.e., BM (black matrix) as shown in broken lines in FIG. 8. This enables the irradiation spot to irradiate the entire area of one pixel.

With the transmittance measurement light source 11 being illuminated, transmitting light intensity of the reference is measured by the CCD camera 17. Further, transmitting light spectrum of the reference may be measured by the spectrometer 18. A measured intensity of the reference is represented by R.

Figure 9:
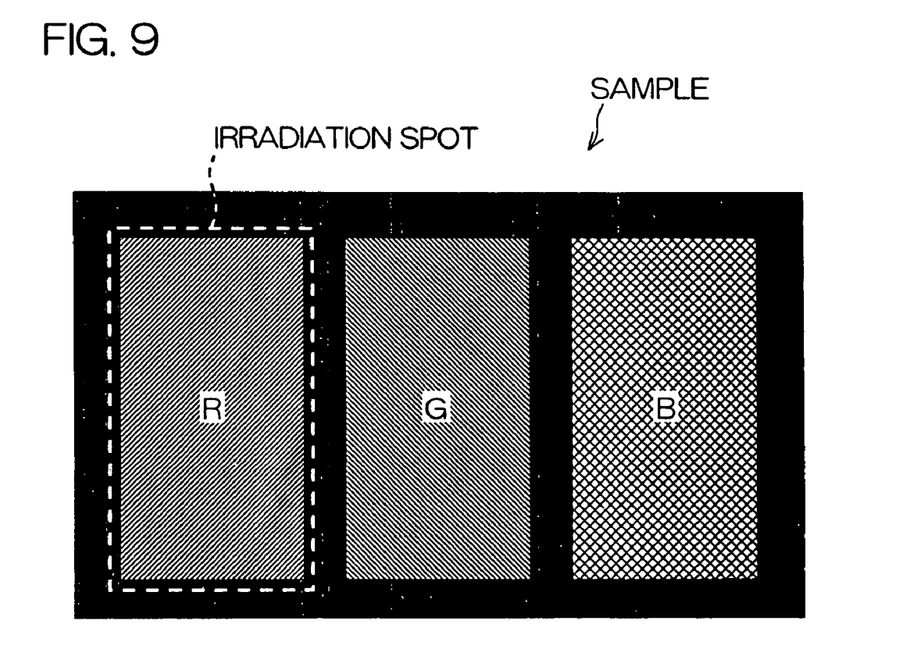
FIG. 9 is a plan view showing a transparent glass plate serving as a sample that is printed in a grid-like black matrix as a frame of each pixel.

Subsequently, as shown in FIG. 9, a sample is prepared such that a transparent glass plate is printed with a grid-like BM (black matrix) pattern forming the frame of one pixel and each pixel of the transparent glass plate is coated with a color filter, and the sample is placed on the sample holder.

Then, the transmittance measurement light source 11 is turned off (Step S9), and the XY stage is operated to move the sample to move onto the optical axis of the lens systems 12a, 12b (Step S10).

The area marker 19 is illuminated (Step S11), and with the lenses of the CCD camera 17 and spectrometer 18 are auto-focused, then the XY stage is operated to move the pixel as the sample to the central position of the area marker 19 (Step S12). Then, the area marker 19 is turned off (Step S13). This enables to place the sample on the optical axis of the CCD camera 17 and spectrometer 18 in the light receiving optical unit.

Then, the transmittance observation light source 15 is turned on to irradiate the entire image area with transmittance observation light from below (Step S14). Then, with colors of R, G, B being recognized by the CCD camera 17, positioning to the center of one of the pixels to be measured, for example, R of R, G, B is carried out by image processing (Step S15). The diameter of the spot of the transmittance observation light source 15 is about φ6 mm, which can include a large number of pixels.

After the positioning is completed, the transmittance observation light source 15 is turned off (Step S16), and the transmittance measurement light source 11 is turned on (Step S17). Then the transmission measurement light source 11 is projected on the sample to measure the light of the sample by CCD camera 17 (Step S18). Further, transmitting light intensity spectrum of the sample may be measured by the spectrometer 18. A measured intensity of the sample is represented by S.

On the other hand, when the sample is measured by the CCD camera 17 under a dark circumstance where all the light sources are off and the aperture is closed, an intensity measured by the CCD camera 17 is represented by D.

Transmittance of the sample can be determined by the following equation:

Transmittance=(S−D)/(R−D)

When D is negligibly small,

T=S/R is satisfied. Thus, a measurement of one sample is completed.

Another sample measurement starts by returning to Step S14, and is carried out such that the entire image area is irradiated with transmittance observation light from below. Then, with colors of R, G, B being recognized by the CCD camera 17, automatic positioning to the center of another one of the pixels to be measured, for example, G of R, G, B is carried out by image processing (Step S15). Then, the transmittance observation light source 15 is turned off (Step S16), and the transmittance measurement light source 11 is turned on (Step S17). Then, the transmission measurement light source 11 is projected on the sample to measure the light of the sample by the CCD camera 17 or the spectrometer 18 (Step S18).

The automatic positioning by image processing enables accurate determination of the shape of the irradiation spot, and error due to the mechanism of the automatically variable aperture unit 13 can be compensated. This enables automatic measurements of the sample and the reference at any designated area.

In this way, a plurality of light of the sample is measured. Once the intensity R of the reference is measured, it does not change in a short time. Therefore, the frequency of measurement of intensity of the reference may be low. For example, measuring light of the reference once in the morning and once in the afternoon would be enough.

Additionally, the aperture variable inspection optical system according to the present invention may be utilized for measurement of reflectance of the sample. In this case, the arrangement of the aperture variable inspection optical system is as shown FIG. 10, in which the light projecting optical unit and the light receiving optical unit are disposed on the same side with respect to the sample.

Figure 10:
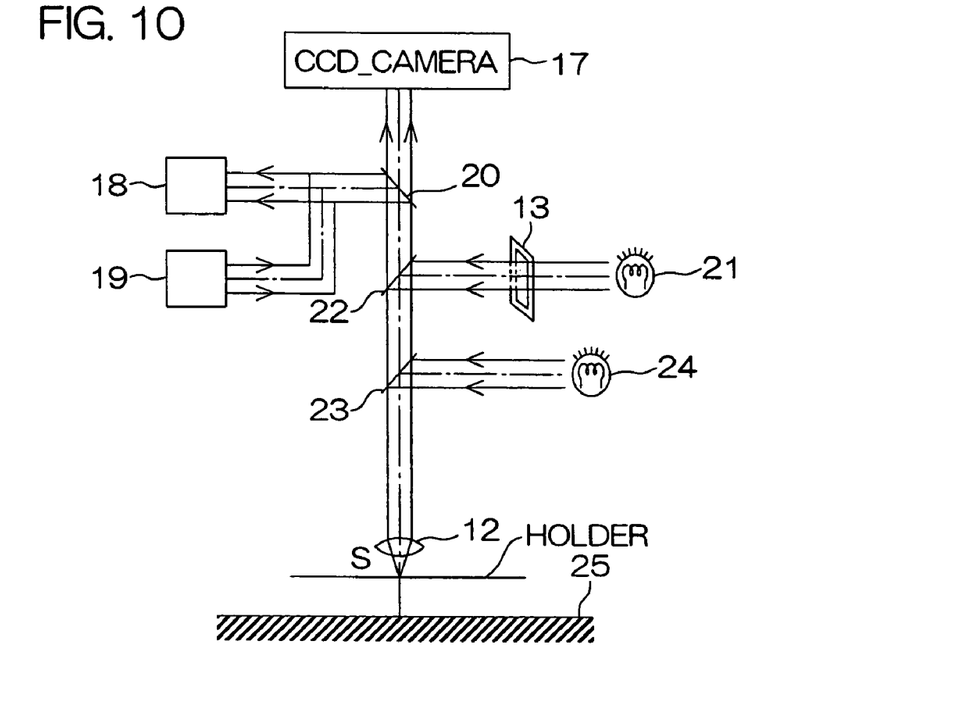
FIG. 10 is a structural diagram of an aperture variable inspection optical system of the present invention when the system is used for measurements of reflectance of sample S.

Light of a reflectance measurement light source 21 for projecting measuring light on a sample S passes through a variable aperture unit 13 interposed between the reflectance measurement light source 21 and the sample S, and passes through a half mirror 22 to be collected on the sample S by a lens system 12. In addition, a half mirror 23 is interposed between the half mirror 22 and the sample S, and a reflectance observation light source 24 for projecting light on the half mirror 23 is provided.

Measurement of reflectance of a sample using this aperture variable inspection optical system will be duly accomplished in the following way.

First, a transparent glass plate printed with a grid-like black matrix forming a frame of each pixel is coated with a material with high reflectance, for example, aluminum or the like. This is used as a reference.

With the pixel serving as the reference positioned at a central position of the screen of the CCD camera 17, the reflectance measurement light source 21 is turned on. Then, the variable aperture unit 13 is controlled to determine the shape (dimensions a, b) of the irradiation spot so that the profile of the irradiation spot covers the frame of one pixel, i.e., BM (black matrix) as shown in broken lines in FIG. 8. This enables the irradiation spot to irradiate the entire area of one pixel.

Reflecting light intensity of the reference is measured by the CCD camera 17. Further, reflecting light intensity spectrum may be measured by the spectrometer 18. A measured intensity of the reference is represented by R'.

Subsequently, the sample is placed under the optical axis of the CCD camera 17 and the spectrometer 18 in the light receiving optical unit, and the reflectance observation light source 24 is turned on to irradiate the entire image area with light (transmission observation light) returning after being reflected by the reflection plate 25. Then, with colors of R, G, B being recognized by the CCD camera 17, positioning to the center of one of the pixels to be measured, for example, R of R, G, B, is carried out by image processing.

After the positioning is completed, the reflectance observation light source 24 is turned off, and the reflectance measurement light source 21 is turned on. With the reflectance measurement light source 21 being projected on the sample, light reflected from the sample is measured by the CCD camera 17. Further, reflection intensity spectrum of the sample may be measured by the spectrometer 18. A measured reflection intensity of the sample is represented by S'.

Reflectance of the sample can be determined by the following equation:

$$\text{Reflectance}=(S'-D)/(R'-D)$$

Figure 11:
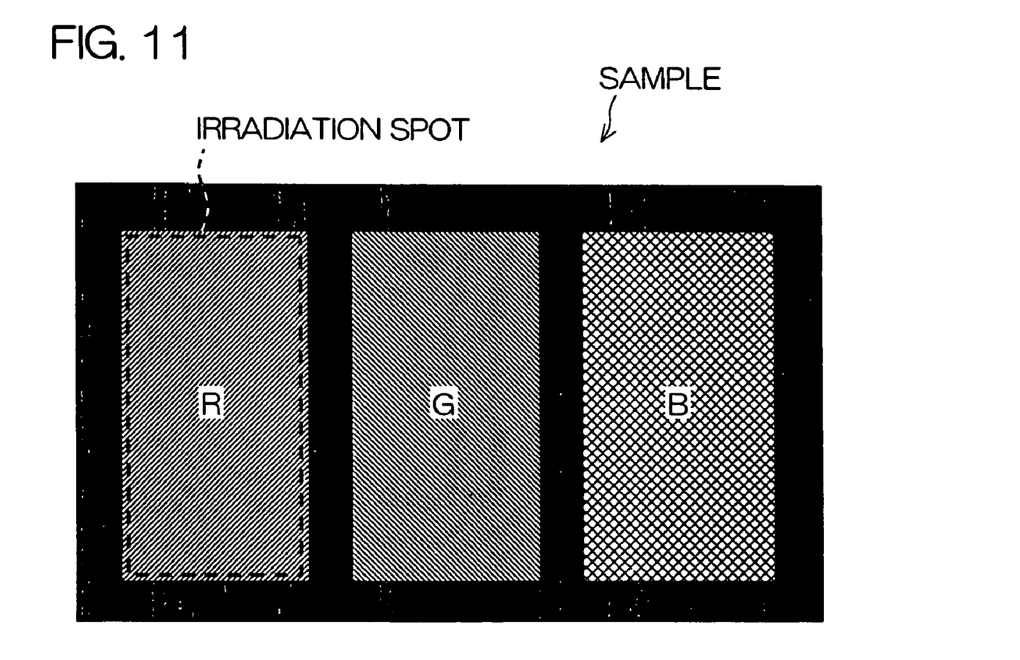
FIG. 11 is a plan view showing a positional relationship between an irradiation spot and a BM when the irradiation spot is incident on the entire area of one pixel while the irradiation spot does not cover the BM.

While specific embodiments of the present invention have been heretofore described, implementation of the present invention is not limited to the foregoing embodiments. For example, while in the embodiments above, transmittance/reflectance are measured with the irradiation spot having a shape that covers the BM for illuminating the entire area of one pixel, the irradiation spot may be formed to have a shape that does not cover the BM as shown in FIG. 11. It is also possible to measure transmittance/reflectance of the entire area of one pixel in the manner shown in FIG. 8. However, when fluctuation in thickness of the color filter in the vicinity of the BM is great, difficulties may arise in controlling chromaticity/transmittance.

Figure 12:
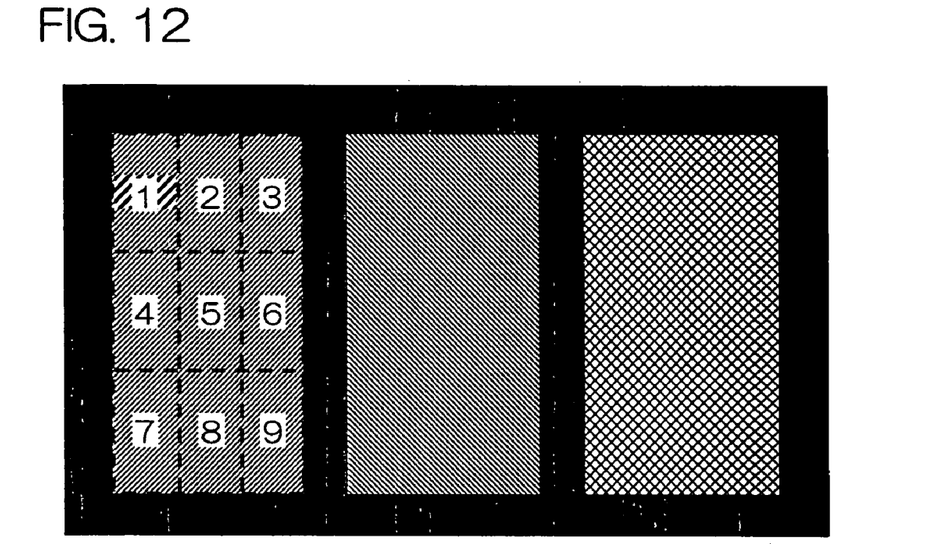
FIG. 12 is a plan view showing a method for evaluating unevenness within one pixel by forming an irradiation spot where one pixel is divided into nine sections.

Instead of the arrangement in which the irradiation spot irradiates the entire area of one pixel, the irradiation spot may be adapted to irradiate a part of one pixel. It is also possible to form an irradiation spot by dividing one pixel into nine sections so that unevenness within one pixel can be evaluated (the number of sections can be optionally determined). This makes it possible to inspect unevenness in optical characteristics within one pixel of a color filter.

Figure 13:
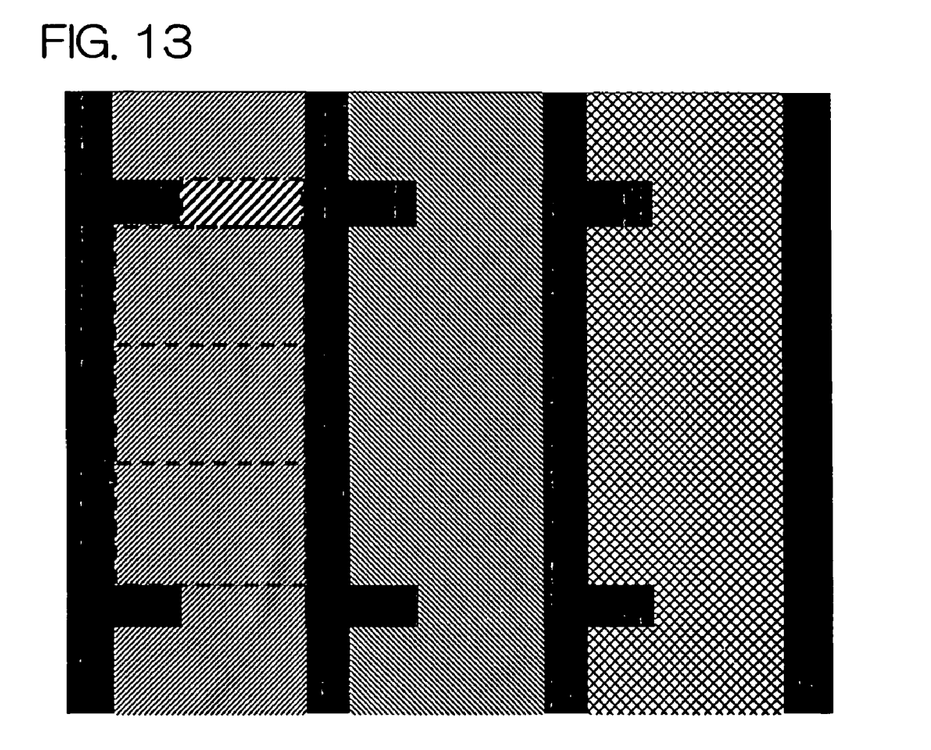
FIG. 13 is a plan view showing a method for evaluating a filter with an irregular shape in which an evaluation is made by a combination of plural times of measurements that are made by changing the position and shape of a quadrangle.

Further, where it is desired to measure a filter with an irregular shape other than quadrangles as shown in FIG. 13, it is possible to carry out plural times of measurements by changing the position and shape of a quadrangle to evaluate using a combination thereof. Other modifications may be also made within the scope of the present invention.

The present application corresponds to Japanese Patent Application No. 2006-234057 filed with Japanese Patent Office on Aug. 30, 2006, and the whole disclosures thereof are incorporated herein by reference.

What is claimed is:

1. A color filter evaluation process performed by projecting light of a measurement light source on a pixel of a color filter as a sample and receiving light from the sample for optical measurement thereof, comprising the steps of:
    (a) preparing a transparent plate including one pixel formed with a frame as a reference, wherein the one pixel is a range covered by a color filter of one color;
    (b) adjusting a size of a light transparent section by a variable aperture unit including the light transparent section whose size is variable so that a profile of an irradiation spot of the measurement light source includes the entire area of the pixel;
    (c) measuring an intensity R of light of the reference with the measurement light source being illuminated;
    (d) preparing a color filter including one pixel formed with a frame as a sample;
    (e) adjusting the size of the light transparent section by the variable aperture unit so that a profile of an irradiation spot of the measurement light source includes the entire area of the pixel;
    (f) measuring an intensity S of light of the sample with the measurement light source being illuminated; and
    (g) calculating a ratio R/S, thereby determining a transmittance of the sample.

2. A color filter evaluation process according to claim 1, wherein the transparent plate serving as the reference is a transparent plate before being coated with a color filter that has only a BM pattern formed thereon.

3. A color filter evaluation process according to claim 1, wherein in the step (b) or (e), the irradiation spot of measurement light source is formed so that the profile thereof covers the frame of the pixel.

* * * * *